United States Patent [19]

Berber et al.

[11] 4,212,539
[45] Jul. 15, 1980

[54] DEVICE FOR GRANULOMETRIC ANALYSIS OF PARTICLES IN FLUIDS

[76] Inventors: Viktor A. Berber, ulitsa Shelkovichnaya, 184, kv. 65; Evgeny S. Pervushin, ulitsa Shelkovichnaya, 182, kv. 71; Vladimir G. Kholin, ulitsa Shelkovichnaya, 184, kv. 53; Alexandr G. Fedorov, poselok Pervomaisky, 6 proezd, 21, kv. 1; Boris M. Galishnikov, ulitsa Shelkovichnaya, 190, kv. 27, all of Saratov, U.S.S.R.

[21] Appl. No.: 933,026

[22] Filed: Aug. 11, 1978

[51] Int. Cl.² .............................................. G01N 15/02
[52] U.S. Cl. ..................................... 356/336; 250/574; 356/339
[58] Field of Search ................. 356/336, 339; 250/564, 250/574

[56] References Cited
U.S. PATENT DOCUMENTS

| 3,493,304 | 2/1970 | Rovner | 356/339 |
| 4,136,953 | 1/1979 | Klein et al. | 356/339 |

*Primary Examiner*—John K. Corbin
*Assistant Examiner*—Matthew W. Koren
*Attorney, Agent, or Firm*—Fleit & Jacobson

[57] ABSTRACT

According to the invention, the device for granulometric analysis of particles contained in fluids comprises a flow-through chamber of an analyzer, a lighting means arranged outside the chamber, opposite a window which is transparent to light and provided in the wall of the chamber, said lighting means being intended to direct a convergent light beam through said window into said chamber, and a light-sensitive means intended to receive light reflected from particles contained in the fluid under investigation and arranged outside said chamber, opposite a second window provided in the wall of the chamber, which second window is transparent to reflected light. The second window is shaped as a cylinder whose axis is matched with the optical axis of the lighting means; the walls of the cylinder serve as walls of the chamber. The optical system of the lighting means is such that the point of intersection of the optical axes of the lighting means and the light-sensitive means is beyond the focus of the lighting means, in the direction of the light flux. The solid angle of the convergent light beam is in this range:

$$0 \leq \alpha \leq 2\text{Arccos}(1/n_1),$$

where $n_1$ is the refractive index of the fluid under investigation.

2 Claims, 2 Drawing Figures

DEVICE FOR GRANULOMETRIC ANALYSIS OF PARTICLES IN FLUIDS

FIELD OF THE INVENTION

The present invention relates to measuring instruments and, more particularly, to devices for granulometric analysis of particles contained in fluids, i.e. devices for measuring the quantity and size of extraneous particles contained in fluids. The invention is applicable to the analysis of low-concentration suspensions, for example, to granulometric analysis of particles of impurities in fuels and lubricants.

BACKGROUND OF THE INVENTION

There is known an optical sensor for determining the quantity of particles in a sample of fluid. The sensor comprises a flow-through cell with two windows. A liquid envelope flows through the cell, and a sample of fluid to be analyzed is introduced into the liquid envelope which separates the samples from particles on the cell walls and accurately directs particles contained in the sample to the focus of a light beam admitted through the windows of the cell.

There is further known a device for granulometric analysis of particles contained in fluids, comprising a flow-through chamber of an analyzer, having an inlet and an outlet. The device further includes a lighting means arranged outside the flow-through chamber, opposite a window which is transparent to light and provided in the wall of the chamber. The lighting means is intended to direct a convergent light beam into the chamber. The device further includes a light-sensitive means to receive light reflected from particles contained in the fluid subjected to granulometric analysis. The light-sensitive means is arranged outside the chamber, opposite a second window provided in the wall of the chamber, which second window is transparent to reflected light. The optical axis of the light-sensitive means extends at a perpendicular to the optical axis of the lighting means and intersects it inside the chamber. The inlet of the chamber communicates with a tubular nozzle arranged in the center of the chamber. Spaced around the tubular nozzle are pipes communicating with a source of pure fluid and intended to produce a liquid envelope that encompasses the flow of the fluid being investigated.

The optical properties of the liquid envelope must be identical with those of the fluid being investigated. This requirement applies to each of the above-mentioned optical sensor and device for granulometric analysis of particles contained in fluids. Identical optical properties of the liquid envelope and fluid under investigation can best be attained when both have the same composition, provided that the fluid used to produce the liquid envelope is pure, i.e. free from all foreign particles with a grain size in excess of the sensitivity threshold of the light-sensitive means. This requirement makes it imperative that the device for granulometric analysis should include such units as a tank for fluid, a pump and a high-performance purifier of fluid. In addition, provision must be made for a special means for equalizing the velocities of the liquid envelope and the fluid being investigated in order to prevent mixing of these flows in the zone of intersection of the fluid being investigated and the light beam, i.e. prevent a transfer of particles from the fluid being investigated to the liquid envelope.

It must further be remembered that a device for granulometric analysis is normally used to analyze different types of fluid. The liquid envelope must be changed each time a different fluid is to be investigated so that its optical properties should correspond to those of the fluid. Such changes significantly affect the rate of analysis and increase the costs involved.

SUMMARY OF THE INVENTION

It is the principal object of the present invention to improve the sensitivity of the device for granulometric analysis of particles contained in fluids.

It is another object of the invention to guarantee a high accuracy of granulometric analysis of particles contained in fluids, while using devices of a simpler design for the purpose.

The foregoing objects of the invention are attained by providing a device for granulometric analysis of particles contained in fluids, comprising a flow-through chamber of an analyzer, having an inlet and an outlet, a lighting means arranged outside the chamber, opposite a window which is transparent to light and provided in the wall of the chamber, the lighting means being intended to direct a convergent light beam into the chamber, and a light-sensitive means to receive light reflected from particles contained in the fluid being investigated, the light-sensitive means being arranged outside the chamber, opposite a second window which is transparent to light and provided in the wall of the chamber, the optical axis of the light-sensitive means extending at a perpendicular to that of the lighting means and intersecting it inside the chamber, the device being characterized, according to the invention, in that the second window is shaped as a cylinder whose axis is matched with the optical axis of the lighting means, the cylinder serving as the walls of the chamber, the optical system of the lighting means being such that the point of intersection of the optical axes of the lighting means and light-sensitive means is beyond the focus of the lighting means in the direction of the light flux, and in that the solid angle $\alpha$ of the convergent light beam arriving into the cylinder is in this range:

$$0 \leq \alpha \leq 2 \operatorname{Arccos}(1/n_1),$$

where $n_1$ is the refractive index of the fluid subjected to granulometric analysis.

In order to exclude losses of useful information, the optical system of the light-sensitive means must be selected with due regard for the location of the region confined within the solid angle of the collimating ray of the light-sensitive means on the internal surface of the cylinder, which must be beyond the line on which that surface is traversed by the light flux emitted by the lighting means, in the direction of the light flux.

The device for granulometric analysis of particles contained in fluids in accordance with the invention makes it possible to investigate impurities in a flow of fluid, while ruling out the reception by the light-sensitive means of light reflected from the walls of the flow-through chamber. This is due to the fact that the solid angle $\alpha$ is selected so as to ensure complete internal reflection of light from the outer walls of the cylinder. This, in turn, minimizes noise currents caused by the light flux passing through the walls of the chamber and the fluid being investigated, i.e. increases the signal-to-noise ratio and guarantees a maximum sensitivity.

Another important feature of the invention is that the light-sensitive means is located so that the region confined within the solid angle of the collimating ray of the light-sensitive means on the internal surface of the cylinder is beyond the line on which that surface is traversed by the light flux emitted by the lighting means, in the direction of the light flux. This feature rules out passage of particles outside the zone exposed to light, i.e. outside the field of vision of the light-sensitive means. This rules out losses of useful information and improves the accuracy of analysis.

BRIEF DESCRIPTION OF THE ACCOMPANYING DRAWINGS

Other objects and advantages of the present invention will become more apparent from the following detailed description of preferred embodiments thereof, taken in conjunction with the accompanying drawings, wherein.

DETAILED DESCRIPTION OF THE INVENTION

Figure 1:
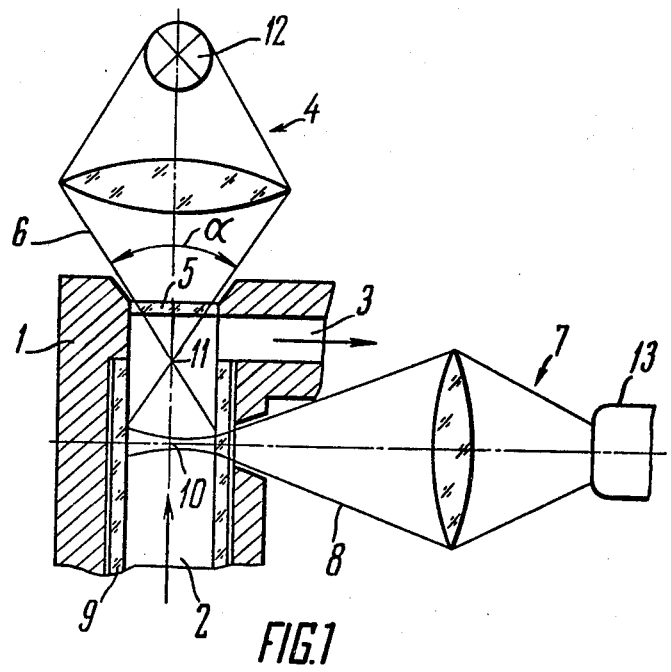
FIG. 1 is a diagram of a device for granulometric analysis of particles contained in fluids, in accordance with the invention.
Figure 2:
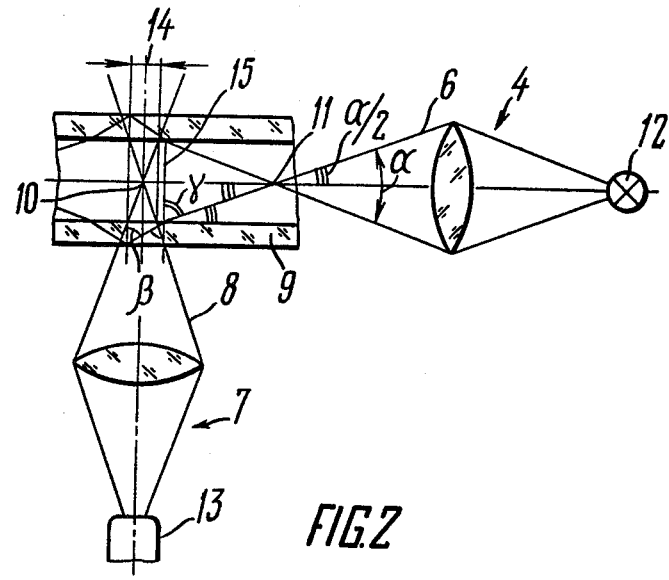
FIG. 2 is a diagram illustrating the way the lighting means and light-sensitive means are arranged with respect to the cylinder of the flow-through chamber, in accordance with the invention.

According to FIGS. 1 and 2, the device for granulometric analysis of particles contained in fluids comprises a flow-through chamber 1 of an analyzer, having an inlet 2 and an outlet 3. The device further includes a lighting means 4 arranged outside the chamber 1, opposite a window 5. The window 5 is transparent to light and provided in the wall of the chamber 1. The lighting means 4 is intended to direct a convergent light beam 6 through the window 5 into the chamber 1. A light-sensitive means 7 is intended to receive a light flux 8 reflected from particles contained in the fluid being investigated. The light-sensitive means 7 is arranged outside the chamber 1, opposite a second window 9 which is transparent to the light flux 8 and provided in the wall of the chamber 1. The optical axis of the light-sensitive means 7 extends at a perpendicular to the optical axis of the lighting means 4 and intersects it inside the chamber 1 at a point 10.

The window 9 is shaped as a cylinder and is further referred to as the cylinder 9. The axis of the cylinder 9 is matched with the optical axis of the lighting means 4. The cylinder 9 performs the function of the walls of the chamber 1, which form the flow of the fluid being investigated. The optical system of the lighting means 4 is selected so that the point 10 of intersection of the optical axes of the lighting means 4 and the light-sensitive means 7 is beyond a focus 11 of the lighting means 4, in the direction of the light flux 6 emitted by a light source 12 of the lighting means 4. The light-sensitive means 7 is provided with a light-sensitive element 13, such as a photoelectron multiplier.

The solid angle $\alpha$ of the convergent light beam 6 is selected within this range:

$$0 \leq \alpha \leq 2 \text{ Arccos } (1/n_1),$$

where $n_1$ is the refractive index of the fluid subjected to granulometric analysis.

The foregoing range is meant to ensure complete internal reflection of light from the outer surface of the cylinder 9:

$$90° \geq \beta \geq \beta_1,$$

where $\beta$ is the angle of incidence of a light beam on the outer surface of the cylinder 9; and $\beta_1$ is the critical angle of incidence, which accounts for complete internal reflection of light from the outer surface of the cylinder 9.

For complete internal reflection, the following condition must be met:

$$\text{Sin } \beta_1 = n_2/n_3 = 1/n_3, \quad (1)$$

where Sin $\beta_1$ is the sine of the critical incidence angle;
$n_2 = 1$ is the refractive index of air; and
$n_3$ is the refractive index of the material of the cylinder 9.

According to the law of refraction of light on the border of the fluid and the material of the cylinder 9, $$n_3 \cdot \text{Sin } \beta_1 = n_1 \cdot \text{Sin } \gamma, \quad (2)$$

where Sin $\gamma$ is the sine of the angle of incidence of light on the internal surface of the cylinder 9.

From (2) we have $$\text{Sin } \gamma = (n_3 - \text{Sin } \beta_1)/n_1 \quad (3)$$

According to FIG. 2, $$\gamma = 90° - (\alpha_1/2), \quad (4)$$

where $\alpha_1$ is the maximum angle of convergence of the light beam which accounts for complete internal reflection of light from the outer surface of the cylinder 9. From 1 we obtain $$\text{Sin } \beta_1 \cdot n_3 = 1. \quad (5)$$

Substituting (4) and (5) into (3), we obtain $$\text{Sin } (90° - \frac{\alpha_1}{n_1}) = \frac{1}{n_1}. \quad (6)$$

From the latter equation we obtain $$\alpha_1 = 2 \text{ Arccos } (1/n_1). \quad (7)$$

The light-sensitive means 7 is so arranged with respect to the cylinder 9 of the flow-through chamber 1 that a region 14, confined within the solid angle of the collimating ray (the light flux 8) of the light sensitive means on the internal surface of the cylinder 9, is beyond a line 15 of intersection of that surface and the convergent light beam 6 emitted by the lighting means 4, in the direction of the light flux.

The device according to the invention for granulometric analysis of particles contained in fluids operates as follows.

The fluid to be investigated is pumped through the chamber 1. As this takes place, the fluid goes from the inlet 2 to the outlet 3 of the chamber 1 and through the transparent cylinder 9 where it is exposed to the light beam 6 arriving from the lighting means 4. When particles of impurities contained in the fluid reach the region 14, i.e. the field of vision of the light-sensitive means 7, they send a pulse of reflected light to the light-sensitive element 13. The magnitude of this pulse is proportional to the particle size. The angle of light reflected by a particle is less than the critical angle of incidence $\beta_1$ which accounts for complete internal reflection of light from the outer surface of the cylinder 9; as a result, the light pulse freely reaches the photoelectron multiplier which produces a corresponding electric pulse to be transmitted to an indicator (not shown). Meanwhile, the light reflected by the walls of the cylinder 9 is not received by the photoelectron multiplier because the angle of incidence of the reflected light on the outer wall of the cylinder 9 is greater than the critical angle $\beta_1$, which accounts for complete internal reflection. This fully eliminates noise currents in the photoelectron multiplier and thus increases the sensitivity.

The region 14 is in the field of vision of the light-sensitive means 7 and is also beyond the line 15 of intersection of the internal surface of the cylinder 9 and the light flux emitted by the lighting means 4; as a result, the region 14 is fully exposed to light, which rules out any loss of useful information.

What is claimed is:

1. A device for granulometric analysis of particles contained in fluids, comprising: a flow-through chamber of an analyzer; an inlet of said flow-through chamber; an outlet of said flow-through chamber; a first window in the wall of said flow-through chamber, which is transparent to a light flux; a lighting means arranged outside said flow-through chamber, opposite said first window, and intended to direct a convergent light beam through said first window into said flow-through chamber; the solid angle $\alpha$ of said convergent light beam being in the range of $0 \leq \alpha \leq 2 \text{ Arccos}(1/n_1)$, where $n_1$ is the refractive index of the fluid subjected to investigation; a light-sensitive means intended to receive light reflected from particles contained in said fluid being investigated, and arranged outside said flow-through chamber; the optical axis of said light-sensitive means extending at a perpendicular to the optical axis of said lighting means and intersecting it inside said flow-through chamber, beyond the focus of said lighting means, in the direction of the light flux; a second window provided in the wall of said flow-through chamber and transparent to light reflected from particles contained in the fluid being investigated, said second window being arranged across the path of reflected light to said light-sensitive means; said second window being shaped as a cylinder whose axis is matched with the optical axis of said lighting means, said cylinder performing the function of the walls of said flow-through chamber.

2. A device as claimed in claim 1, wherein the optical system of said light-sensitive means is such that the region, confined within the solid angle of the collimating ray of said light-sensitive means on the internal surface of said cylinder, is beyond the line of intersection of that surface and the light flux emitted by said lighting means, in the direction of the light flux.

* * * * *